United States Patent [19]

Petrzilka et al.

[11] Patent Number: 4,630,896

[45] Date of Patent: Dec. 23, 1986

[54] BENZONITRILES

[75] Inventors: Martin Petrzilka, Kaiseraugst; Alois Villiger, Basel, both of Switzerland

[73] Assignee: Hoffmann-La Roche Inc., Nutley, N.J.

[21] Appl. No.: 614,622

[22] Filed: May 29, 1984

[30] Foreign Application Priority Data

Jun. 17, 1983 [CH] Switzerland .................... 3334/83

[51] Int. Cl.$^4$ .................... C09K 3/34; G02F 1/13; C07C 121/60; C07C 120/00
[52] U.S. Cl. .................... 350/350 R; 252/299.5; 252/299.63; 350/350 S; 558/411; 558/423
[58] Field of Search ............... 252/299.63; 350/350 R, 350/350 S; 260/465 R, 465 C, 465 F; 255/299.5

[56] References Cited

U.S. PATENT DOCUMENTS

| | | | |
|---|---|---|---|
| 4,035,055 | 7/1977 | Coates et al. | 252/299.66 |
| 4,149,413 | 4/1979 | Gray et al. | 252/299.67 |
| 4,222,887 | 9/1980 | Matsufuji | 252/299.63 |
| 4,229,315 | 10/1980 | Krause et al. | 252/299.63 |
| 4,261,651 | 4/1981 | Gray et al. | 252/299.63 |
| 4,393,258 | 7/1983 | Sato et al. | 252/299.5 |
| 4,398,803 | 8/1983 | Pohl et al. | 252/299.01 |
| 4,400,293 | 8/1983 | Romer et al. | 252/299.63 |
| 4,419,263 | 12/1983 | Praefcke et al. | 252/299.63 |
| 4,431,853 | 2/1984 | Sato et al. | 252/299.63 |
| 4,439,015 | 3/1984 | Rich et al. | 252/299.63 |
| 4,455,443 | 6/1984 | Takatsu et al. | 252/299.5 |
| 4,482,472 | 11/1984 | Carr et al. | 252/299.5 |
| 4,514,044 | 4/1985 | Gunjima et al. | 252/299.5 |
| 4,528,114 | 7/1985 | Petrzilka et al. | 252/299.6 |
| 4,556,745 | 12/1985 | Carr et al. | 252/299.6 |
| 4,558,151 | 12/1985 | Takatsu et al. | 252/299.63 |
| 4,565,425 | 1/1986 | Petrzilka et al. | 252/299.63 |
| 4,583,826 | 4/1986 | Petrzilka et al. | 252/299.63 |

FOREIGN PATENT DOCUMENTS

| | | | |
|---|---|---|---|
| 58512 | 8/1982 | European Pat. Off. | 252/299.62 |
| 102047 | 3/1984 | European Pat. Off. | 252/299.63 |
| 3040632 | 5/1982 | Fed. Rep. of Germany | 252/299.63 |
| 3226051 | 2/1983 | Fed. Rep. of Germany | 252/299.63 |
| 3237367 | 3/1983 | Fed. Rep. of Germany | 252/299.63 |
| 3233641 | 3/1983 | Fed. Rep. of Germany | 252/299.63 |
| 3317597 | 11/1984 | Fed. Rep. of Germany | 252/299.63 |
| 59-110631 | 6/1984 | Japan | 252/299.63 |
| 2092169 | 8/1982 | United Kingdom | 252/299.63 |
| 2107733 | 5/1983 | United Kingdom | 252/299.63 |
| 2134110 | 8/1984 | United Kingdom | 252/299.63 |

OTHER PUBLICATIONS

Osman, M. A., et al., Mol. Cryst. Liq. Cryst., vol. 82 (letters) pp. 339–344 (Jan. 1983).
Gray, G. W., "Liquid Crystal Compounds Incorporated the Trans-1, 4-Substituted Cyclohexane Ring System," Mol. Cryst. Liq. Cryst., 1979, vol. 53, pp. 147–166.
Mol. Cryst. Liq. Cryst. 102:345 (1983).

Primary Examiner—Teddy S. Gron
Attorney, Agent, or Firm—Jon S. Saxe; Bernard S. Leon; George W. Johnston

[57] ABSTRACT

Compounds of the formula:

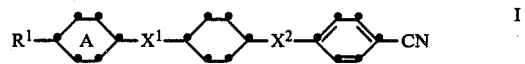

wherein
one of $X^1$ and $X^2$ is —CH$_2$CH$_2$— and the other is —CH$_2$CH$_2$— or a single covalent bond,
ring A is 1,4-phenylene or trans-1,4-cyclohexylene, and
$R^1$ is straight-chain C$_1$–C$_{12}$-alkyl or when positioned on a 1,4-phenylene ring $R^1$ may also be straight chain C$_1$–C$_{12}$-alkoxy.

6 Claims, No Drawings

BENZONITRILES

BACKGROUND OF THE INVENTION

1. Field of the Invention

This invention relates to liquid crystal compounds and mixtures containing same. This invention also relates to the manufacture of these compounds and their use for electro-optical and chromatographic purposes.

2. Background Description

Liquid crystalline materials are of importance primarily as dielectrics in electro-optical indicating devices, since the optical properties of such materials can be influenced by an electric field. Electro-optical devices based on liquid crystals are well known to the person skilled in the art and can be based on various effects such as, for example, dynamic scattering, the deformation of aligned phases (DAP type), the Schadt-Helfrich effect (rotation cell), a cholesteric-nematic phase transition or the guest/host effect ("guest/host cell").

For a successful technical application of these effects it is, however, important that the materials used satisfy a number of additional requirements. For example, they must have a good chemical stability towards heat, moisture, air, electromagnetic radiation (in the ultraviolet, visible and infrared region), electric fields and the like, they must be colourless and they must give a good contrast when used in a cell. Further, they should have a low viscosity and short response times and should have a nematic or cholesteric mesophase in the entire temperature range in which the liquid crystal cell is to be operated. Other properties such as, for example, the dielectric anisotropy, the threshold potential and the conductivity must fulfil different conditions depending on the type of cell which is used.

Since, in general, it is not possible to achieve all of the desired and to some extent contradictory properties with a single compound, mixtures of two or more compounds are manufactured as a rule. In this case, however, it has to be taken into consideration that the components must not undergo chemical reactions with one another and also that they must have good miscibility at room temperature and lower temperatures. Further, the mixtures should have no smectic mesophases, at least at temperatures at which the liquid crystal cell is to be operated.

Liquid crystals with positive dielectric anisotropy ($\Delta\epsilon = \epsilon_\parallel - \epsilon_\perp > 0$, $\epsilon_\parallel$ signifying the dielectric constant along the longitudinal molecular axis and $\epsilon_\perp$ signifying the dielectric constant perpendicular thereto) orientate themselves in an electric field with the direction of the largest dielectric constant, i.e. with the longitudinal molecular axis, parallel to the field direction. This effect is used, inter alia, in the aforementioned rotation cell and guest/host cell. In order to maintain a low threshold potential, the liquid crystal material used in this case should have a relatively high anisotropy of the dielectric constants. On the other hand, however, compounds with a large positive anisotropy of the dielectric constants generally have the disadvantage that at the same time they increase the viscosity of the liquid crystal material.

SUMMARY OF THE INVENTION

The present invention concerns compounds of the formula:

wherein one of the symbols $X^1$ and $X^2$ signifies —CH$_2$CH$_2$— and the other signifies —CH$_2$CH$_2$— or a single covalent bond, ring A signifies 1,4-phenylene or trans-1,4-cyclohexylene and $R^1$ signifies straight-chain $C_1$–$C_{12}$-alkyl or when positioned on a 1,4-phenylene ring $R^1$ may also be a straight-chain $C_1$–$C_{12}$-alkoxy;

as well as liquid crystalline mixtures containing such compounds. The present invention also concerns the manufacture of these compounds and their use for electro-optical and chromatographic purposes.

The compounds of the invention have at the same time large positive anisotropies of the di-electric constants and high clearing points in spite of comparatively low viscosities. They are colourless, they have a very good chemical and photochemical stability and they also have the remaining requisite properties. Since they have good miscibility with other liquid crystals, they have a broad field of application.

Further, the compounds of the invention can also be used for or as stationary phases in gas chromatography. In particular, they are suitable for the separation of isomer mixtures (e.g. cis/trans-disubstituted cyclohexanes, double bond isomers and the like).

DETAILED DESCRIPTION OF THE INVENTION

The present invention concerns compounds of the formula:

wherein one of $X^1$ and $X^2$ is —CH$_2$CH$_2$— and the other is —CH$_2$CH$_2$— or a single covalent bond, ring A is 1,4-phenylene or trans-1,4-cyclohexylene and $R^1$ is straight-chain $C_1$–$C_{12}$-alkyl or when positioned on a 1,4-phenylene ring $R^1$ may also be a straight-chain $C_1$–$C_{12}$-alkoxy;

The present invention also relates to liquid crytalline mixtures containing such compounds of formula I. The present invention also concerns the manufacture of these compounds and their use for electro-optical and chromatographic purposes.

The compounds of the invention have at the same time large positive anisotropies of the di-electric constants and high clearing points in spite of comparatively low viscosities. They are colourless, they have a very good chemical and photochemical stability and they also have the remaining requisite properties. Since they have good miscibility with other liquid crystals, they have a broad field of application.

Further, the compounds of the invention can also be used for or as stationary phases in gas chromatography. In particular, they are suitable for the separation of isomer mixtures (e.g. cis/trans-disubstituted cyclohexanes, double bond isomers and the like).

Unless otherwise stated, "alkyl" denotes a straight-chain alkyl group of 1 to 12 carbon atoms or a branched-chain alkyl group of 1 to 12 carbon atoms. Exemplary straight-chain alkyl groups are methyl, ethyl, propyl, butyl, pentyl, hexyl, heptyl, octyl, nonyl, decyl, undecyl and dodecyl. Exemplary branched-chain alkyl grous are isopropyl, isobutyl, sec-butyl, 1-methylbutyl, 2-methylbutyl, 3-methylpentyl, 4-methylhexyl and isopentyl.

The term "alkoxy" as well as any other groups in the specification containing "alkyl" denote moieties in which their "alkyl" portions are as defined previously. In particular, straight-chain alkoxy groups denote moieties having a straight-chain alkyl portion as previously defined. Exemplary straight-chained alkoxy groups are methoxy, ethoxy, propyloxy, butyloxy, pentyloxy, hexyloxy, heptyloxy.

Unless otherwise stated, the term "halogen" or "halide" denotes fluorine, chlorine bromine, or iodine.

Preferred compounds are those in which $X^1$ is —$CH_2CH_2$— and $X^2$ is a single covalent bond; or $X^1$ and $X^2$ are both —$CH_2CH_2$—.

Other preferred compounds of formula I are those in which the $R^1$ is straight-chain $C_1$-$C_7$-alkyl or straight-chain $C_1$-$C_6$-alkoxy. Further, more preferred are those compounds of formula I in which $R^1$ is a straight-chain alkyl or when ring A is 1,4 phenylene ring, $R^1$ is a $C_1$-$C_6$ alkoxy.

Formula I above embraces p-[trans-4-[2-(p-alkylphenyl or p-alkoxyphenyl)ethyl]cyclohexyl]benzonitriles, p-[trans-4-[2-(trans-4-alkylcyclohexyl)ethyl]cyclohexyl]benzonitriles, p-[2-[trans-4-(p-alkylphenyl or p-alkoxyphenyl)cyclohexyl]ethyl]benzonitriles, p-[2-[trans-4-(trans-4-alkylcyclohexyl)cyclohexyl]ethyl]benzonitriles, p-[2-[trans-4-[2-(p-alkylphenyl or p-alkoxyphenyl)ethyl]cyclohexyl]ethyl]benzonitriles and p-[2-[trans-4-[2-(trans-4-alkylcyclohexyl)ethyl]cyclohexyl]ethyl]benzonitriles, wherein alkyl signifies in each case methyl, ethyl, propyl, butyl, pentyl, hexyl, heptyl, octyl, nonyl, decyl, undecyl and dodecyl and alkoxy signifies in each case methoxy, ethoxy, propyloxy, butyloxy, pentyloxy, hexyloxy, heptyloxy, octyloxy, nonyloxy, decyloxy, undecyloxy and dodecyloxy.

The compounds of formula I can be manufactured in accordance with the invention by (a) for the manufacture of the compounds of formula I in which $X^2$ signifies an ethylene group, catalytically hydrogenating a compound of the formula:

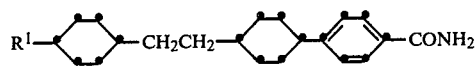

wherein $X^1$ signifies —$CH_2CH_2$— or a single covalent bond and ring A and $R^1$ have the significances given above,
or (b) for the manufacture of the compounds of formula I in which $X^1$ signifies an ethylene group, $X^2$ signifies a single covalent bond and ring A signifies 1,4-phenylene, catalytically hydrogenating a compound of the formula:

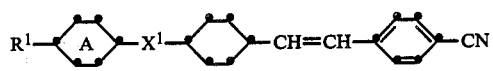

wherein $R^1$ has the significance given above,
or (c) for the manufacture of the compounds of formula I in which $X^1$ signifies an ethylene group, $X^2$ signifies a single covalent bond and ring A signifies trans-1,4-cyclohexylene, dehydrating a compound of the formula:

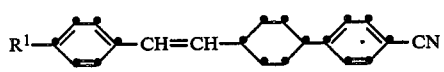

wherein $R^1$ has the significance given above.

The catalytic hydrogenation of the compounds of formulae II and III can be carried out in a manner known per se with any usual hydrogenation catalyst such as palladium, platinum, Raney-nickel and the like, preferably with palladium. As the solvent there is conveniently used a non-polar inert organic solvent, for example a saturated ether or ester or, preferably, a saturated or aromatic hydrocarbon such as hexane, toluene and the like. The temperature and pressure are not critical. The catalytic hydrogenation is conveniently carried out at a temperature between room temperature and the boiling point of the mixture and at a pressure of about 1–5 atmospheres.

The dehydration of an amide of formula IV can also be carried out in a manner known per se. Suitable dehydrating agents are, for example, phosphorus oxychloride, phosphorus pentoxide, thionyl chloride, acetic anhydride and especially benzenesulphonyl chloride. If desired, the dehydration can be carried out in an inert organic solvent (e.g. a hydrocarbon or a halogenated hydrocarbon) and/or in the presence of a base (e.g. pyridine or triethylamine). The temperature and pressure are not critical. However, the dehydration is preferably carried out at about 50° C. up to the reflux temperature of the mixture and at atmospheric pressure.

The compounds of formulae II-IV are novel and are also objects of the present invention. They can be prepared in a manner known per se from known compounds.

For example, the compounds of formula II can be prepared by a Wittig reaction from a p-cyanobenzyl-triphenylphosphonium halide and a suitable cyclohexanecarboxaldehyde. The cyclohexanecarboxaldehydes are obtainable from the corresponding known cyclohexanecarbonitriles by reduction with diisobutylaluminium hydride.

The compounds of formula III can be prepared, for example, by a Wittig reaction from 4-(p-cyanophenyl)-cyclohexanecarboxaldehyde and a p-(alkyl or alkoxy)-benzyl-triphenylphosphonium halide. 4-(p-Cyanophenyl)cyclohexanecarboxaldehyde is obtainable from 4-(p-cyanophenyl)cyclohexanone by reaction with methoxymethyl-triphenylphosphonium chloride and subsequent hydrolysis of the enol ether.

The compounds of formula IV can be prepared, for example, by reacting a 2-(trans-4-alkylcyclohexyl)ethyl-triphenylphosphonium halide in a Wittig reaction with 4-(p-cyanophenyl)cyclohexanone, subjecting the unsaturated nitrile obtained to saponification and subsequent catalytic hydrogenation in the presence of palladium, converting the saturated carboxylic acid obtained into the acid chloride (e.g. with thionyl chloride) and finally reacting the acid chloride with ammonia. A further method for the preparation of the compounds of formula IV comprises reacting a 2-(trans-4-alkylcyclohexyl)ethyl-triphenylphosphonium halide in a Wittig reaction with 4-phenylcyclohexanone, catalytically hydrogenating the compound obtained in the presence of palladium, converting the product by Friedel-Crafts acylation with acetyl chloride in the presence of aluminium trichloride and subsequent reaction with hypohalite (e.g. sodium hypochlorite) into the carboxylic acid and finally converting the latter into the desired amide as mentioned above via the acid chloride. The 2-(trans-4-alkylcyclohexyl)ethyl-triphenylphosphonium halides can be obtained by reacting a trans-4-alkylcyclohexanecarboxaldehyde with methoxymethyltriphenylphosphonium chloride, hydrolyzing the enol ether, reducing the aldehyde with sodium borohydride and finally converting the alcohol obtained into the phosphonium salt via the halide.

The liquid crystalline mixtures in accordance with the invention contain at least two components of which at least one component is a compound of formula I. In addition to one or more compounds of formula I the mixtures in accordance with the invention can contain one or more additional suitable liquid crystalline or non-liquid crystalline substances such as, for example, substances from the classes of Schiff's bases, azobenzenes, azoxybenzenes, esters with 2-5 carbocyclic rings, biphenyls, terphenyls, phenylcyclohexanes, cyclohexylbiphenyls, pyrimidines, dioxanes, bicyclooctanes, ethane derivatives with 2-4 carbocyclic rings and the like. Such substances are known to the person skilled in the art and many of them are, moreover, commercially available.

The liquid crystal mixtures provided by the invention preferably contain one or more compounds of formula I and one or more compounds of the following formulae:

  V

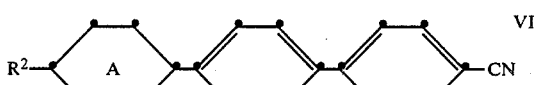  VI

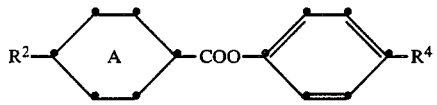  VII

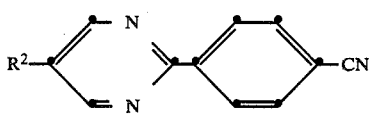  VIII

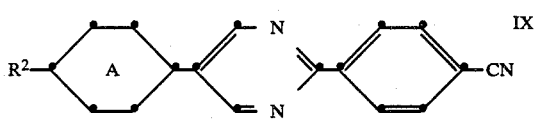  IX

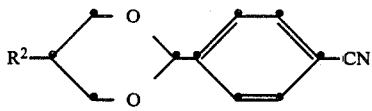  X

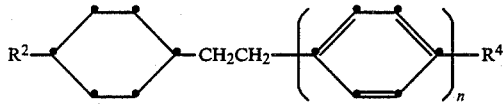  XI

  (blank)

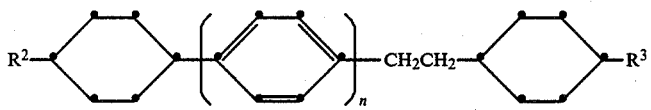  XII

  (blank)

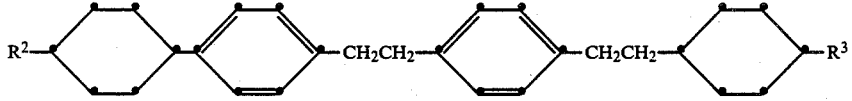  XIII

  (blank)

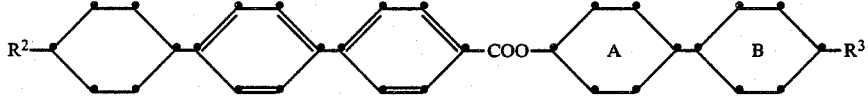  XIV

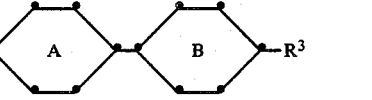  (blank)

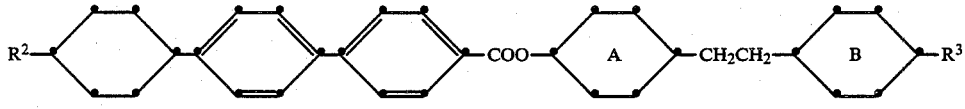  XV

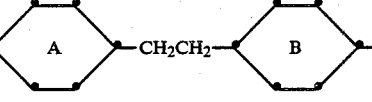  (blank)

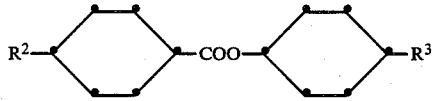  XVI

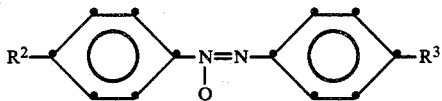  XVII

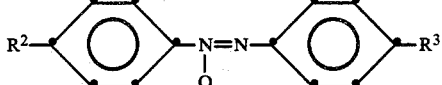

wherein each of $R^2$ and $R^3$ is straight-chain $C_1$–$C_7$-alkyl, $R^4$ is cyano, straight-chain $C_1$–$C_7$-alkyl or straight-chain $C_1$–$C_7$-alkoxy, n is the integer 1 or 2 and each of rings A and B is 1,4-phenylene or trans-1,4-cyclohexylene.

The mixtures provided by the invention can contain suitable optically active compounds (e.g. optically active biphenyls) and/or dichroic colouring substances (e.g. azo, azoxy and anthraquinone colouring substances). The amount of such compounds is determined by the solubility and the desired pitch, colour, extinction and the like. Preferably, the amount of optically active compounds is at most about 4% by weight and the amount of dichroic colouring substances is at most about 10% by weight.

The amount of compounds of formula I in the mixtures provided by the invention can vary in wide limits. The mixtures provided by the invention can consist of two or more compounds of formula I. In general, however, they contain at least about 1% by weight and at most about 25% by weight of compounds of formula I. The amount of compounds of formula I is preferably about 3–15% by weight.

The manufacture of the liquid crystalline mixtures and of the electro-optical devices can be carried out in a manner known per se.

The use of the compounds provided by the invention for or as liquid crystalline stationary phases in gas chromatography can be carried out in a manner known per se and on usual carrier materials. The compounds provided by the invention are especially suitable for the separation of isomer mixtures which can not be separated or which can be separated only with difficulty using conventional stationary phases.

The invention is also concerned with all novel compounds, mixtures, processes, uses and devices as herein described.

The following Examples illustrate the manufacture of the compounds provided by the invention, and the preparation of certain starting materials. Unless otherwise stated, percentages and ratios relating to solvent mixtures are expressed in volume, purity data determined by gas chromatography are expressed in area %, and the remaining percentages and ratios are expressed in weight. Temperatures are in degrees Celsius (°C.), normal pressure is about 1 atmosphere, and room temperature is about 23° C. In the Examples C denotes a crystalline phase, S denotes a smectic phase, N denotes a nematic phase, and I denotes the isotropic phase. Unless indicated otherwise, the Examples were carried out as written.

EXAMPLE 1

6.0 g of p-[2-[trans-4-[2-(trans-4-propylcyclohexyl)ethyl]cyclohexyl]vinyl]benzonitrile were dissolved in 400 ml of hexane and hydrogenated with 0.8 g of palladium/carbon (10%) at room temperature and normal pressure until the hydrogen uptake came to a standstill. After filtering off the catalyst, the p-[2-[trans-4-[2-(trans-4-propylcyclohexyl)ethyl]cyclohexyl]ethyl]benzonitrile was recrystallized twice from hexane; m.p. (C—N) 91.5° C., cl.p. (N—I) 167° C.

The p-[2-[trans-4-[2-(trans-4-propylcyclohexyl)ethyl]cyclohexyl]vinyl]benzonitrile used as the starting material was prepared as follows:

(a) 24 ml of a 1.2M solution of diisobutylaluminium hydride in toluene were added dropwise over a period of 30 minutes at 0° C. and under an inert gas atmosphere to a solution of 5.5 g of trans-4-[2-(trans-4-propylcyclohexyl)ethyl]cyclohexanecarbonitrile in 500 ml of toluene. The mixture was stirred at 0° C. for another hour and then at room temperature for 3 hours. The mixture was subsequently poured into 500 ml of 0.5N sulphuric acid and extracted three times with 200 ml of diethyl ether each time. The combined organic phases were washed first with saturated sodium hydrogen carbonate solution and then with water, dried over sodium sulphate and concentrated, thereby obtaining 5.6 g of trans-4-[2-(trans-4-propylcyclohexyl)ethyl]cyclohexanecarboxaldehyde.

(b) A mixture of 5.6 g of trans-4-[2-(trans-4-propylcyclohexyl)ethyl]cyclohexanecarboxaldehyde, 10.6 g of p-cyanobenzyl-triphenylphosphonium bromide and 200 ml of dioxan was treated with 14.5 g of powdered potassium carbonate and the mixture was heated to boiling for 72 hours. After cooling, the mixture was filtered, the filtrate was concentrated and the residue was chromatographed on silica gel with hexane/diethyl ether (vol. 4:1), thereby obtaining 6.0 g of p-[2-[trans-4-[2-(trans-4-propylcyclohexyl)ethyl]cyclohexyl]vinyl]benzonitrile.

EXAMPLE 2

7.0 g of p-[4-[2-(p-pentylphenyl)vinyl]cyclohexyl]benzonitrile were dissolved in 350 ml of toluene, treated with 1.4 g of palladium/carbon (10%) and hydrogenated at room temperature and normal pressure until the hydrogen uptake came to a standstill. The crude p-[trans-4-[2-(p-pentylphenyl)ethyl]cyclohexyl]benzonitrile obtained after filtering off the catalyst and concentrating the filtrate was recrystallized twice from ethanol. Yield 4.2 g; m.p. (C—N) 61.5° C., cl.p. (N—I) 126° C.

The p-[4-[2-(p-pentylphenyl)vinyl]cyclohexyl]benzonitrile used as the starting material was prepared as follows:

(a) A suspension of 27.9 g of methoxymethyl-triphenylphosphonium chloride in 200 ml of dry t-butyl methyl ether was treated portionwise at −10° C. over a period of 10 minutes under an inert gas atmosphere while stirring with 9.5 g of potassium t-butylate. After another 30 minutes, a solution of 10.8 g of 4-(p-cyanophenyl)cyclohexanone in 125 ml of dry tetrahydrofuran was added to the deep orange mixture at 0°–5° C.

The mixture was stirred at 0° C. for another 30 minutes and at room temperature for 2.5 hours, then poured into 1200 ml of hexane and filtered. The filtrate was concentrated and the residue was chromatographed on silica gel with hexane/ethyl acetate (vol. 95:5). The fractions of p-[4-(methoxymethylidene)cyclohexyl]benzonitrile which were pure according to thin-layer chromatography were concentrated, there being obtained 11.0 g of a colourless oil.

(b) The resulting oil (11.0 g) of p-[4-(methoxymethylidene)cyclohexyl]benzonitrile was heated to boiling for 1 hour in a mixture of 200 ml of tetrahydrofuran and 50 ml of 2N hydrochloric acid. The mixture was subsequently poured on to 500 ml of ice/water and extracted three times with 200 ml of diethyl ether each time. The organic phases were washed neutral with water, dried over sodium sulphate and concentrated, thereby obtaining 10.0 g of colourless and in part solid 4-(p-cyanophenyl)cyclohexanecarboxaldehyde (cis/trans ratio about 1:3).

(c) A mixture of 4.6 g of the 4-(p-cyanophenyl)cyclohexanecarboxaldehyde obtained, 15 g of powdered potassium carbonate, 16.2 g of p-pentylbenzyl-triphenylphosphonium bromide and 300 ml of dioxan was heated to boiling for 72 hours. After cooling, the mixture was filtered and the filtrate was concentrated. The residue was suspended in 400 ml of hexane and freed from insoluble triphenylphosphine oxide by filtration. The filtrate was concentrated and the crude product obtained was purified by chromatography on silica gel with hexane/ethyl acetate (vol. 95:5). There were thus obtained 7.0 g of p-[4-[2-(p-pentylphenyl)vinyl]cyclohexyl]benzonitrile (cis/trans ratio at the cyclohexane ring about 15:85, E/Z ratio about 85:15).

The following compound was manufactured in an analogous manner using 4-(p-pentylphenyl)cyclohexanone in place of 4-(p-cyanophenyl)cyclohexanone and p-cyanobenzyl-triphenylphosphonium bromide in place of p-pentylbenzyl-triphenylphosphonium bromide:

p-[2-[Trans-4-(p-pentylphenyl)cyclohexyl]ethyl]benzonitrile; m.p. (C—N) 77.5° C., cl.p. (N—I) 120° C.

EXAMPLE 3

1.85 g of benzenesulfonyl chloride were added to a suspension of 2.6 g of crude p-[trans-4-[2-(trans-4-pentylcyclohexyl)ethyl]cyclohexyl]benzamide in 50 ml of pyridine and the mixture was stirred at 55° C. overnight. The solution obtained was poured into water and the product was extracted with diethyl ether. The ether extract was washed four times with 50 ml of 3N hydrochloric acid each time, once with 50 ml of saturated sodium hydrogen carbonate solution and three times with 100 ml of water each time, dried over sodium sulphate and concentrated. The crude p-[trans-4-[2-(trans-4-pentylcyclohexyl)ethyl]cyclohexyl]benzonitrile (2.4 g) was recrystallized three times from hexane; yield 1.1 g; m.p. (C—N) 61.5° C. or 67° C. (two modifications), cl.p. (N—I) 193° C.

The p-[trans-4-[2-(trans-4-pentylcyclohexyl)ethyl]cyclohexyl]benzamide used as the starting material was prepared as follows:

(a) In a manner analogous to that described in Example 2, paragraphs (a) and (b), trans-4-pentylcyclohexanecarboxaldehyde was reacted in a Wittig reaction with methoxymethyl-triphenylphosphonium chloride and potassium t-butylate and the resulting enol ether was subsequently hydrolyzed in tetrahydrofuran/2N hydrochloric acid to give (trans-4-pentylcyclohexyl)acetaldehyde.

(b) A mixture of 35.1 g of (trans-4-pentylcyclohexyl)acetaldehyde and 400 ml of ethanol/water (vol. 1:1) was treated portionwise with 36 g of sodium borohydride and stirred for another 1 hour. The mixture was then poured into 1200 ml of water and extracted three times with 400 ml of diethyl ether each time. The organic phases were washed neutral with water, dried over sodium sulphate and concentrated. Yield: 34.2 g of 2-(trans-4-pentylcyclohexyl)ethanol as a yellowish oil.

(c) A mixture of 20 g of 2-(trans-4-pentylcyclohexyl)ethanol, 27.5 g of triphenylphosphine and 350 ml of dichloromethane was treated portionwise while stirring at −30° C. over a period of 45 minutes under an inert gas atmosphere with 36.5 g of tetrabromomethane. The resulting mixture was then stirred at −20° C. for another 30 minutes and at room temperature for 5 hours. The mixture was subsequently concentrated and the residue was triturated with 500 ml of hexane. After cooling to 0° C., the precipitated triphenylphosphine oxide was filtered off and the filtrate was chromatographed on silica gel with hexane. The crude 1-bromo-2-(trans-4-pentylcyclohexyl)ethane obtained (29.0 g) was distilled at 92°-98° C./1.5 Torr. Yield: 21.9 g as a colourless oil.

(d) A mixture of 13.0 g of 1-bromo-2-(trans-4-pentylcyclohexyl)ethane, 16.0 g of triphenylphosphine and 375 ml of xylene was heated to boiling for 60 hours. After cooling to 5° C., the precipitated product was filtered off under suction, washed with toluene and hexane and dried, there being obtained 15.0 g of 2-(trans-4-pentylcyclohexyl)ethyl-triphenylphosphonium bromide; m.p. 183°-185° C.

(e) A suspension of 10.6 g of 2-(trans-4-pentylcyclohexyl)ethyl-triphenylphosphonium bromide in 100 ml of dry t-butyl methyl ether was treated portionwise under an inert gas atmosphere at 5°-10° C. with 2.2 g of potassium t-butylate and the mixture was stirred for a further 10 minutes. Subsequently, a solution of 3.5 g of 4-(p-cyanophenyl)cyclohexanone in 50 ml of tetrahydrofuran was added dropwise over a period of 30 minutes to the orange suspension. The mixture was stirred at room temperature overnight and then treated with 50 ml of water. The aqueous phase was separated and extracted with diethyl ether. The combined organic phase was washed neutral with water, dried over sodium sulphate and concentrated. The residue was chromatographed on silica gel with hexane/ethyl acetate (vol. 95:5), thereby obtaining 3.8 g of p-[4-[2-(trans-4-pentylcyclohexyl)ethylidene]cyclohexyl]benzonitrile.

(f) A mixture of 3.5 g of crude p-[4-[2-(trans-4-pentylcyclohexyl)ethylidene]cyclohexyl]benzonitrile and 100 ml of ethylene glycol was treated with 2.0 g of potassium hydroxide and the resulting mixture was then heated to slight boiling at a bath temperature of 190° C. for 7 hours. After cooling, the mixture was poured into water and acidified with 3N hydrochloric acid. The precipitated product was taken up in diethyl ether. The ether extract was washed three times with 100 ml of water each time, dried over sodium sulphate and concentrated. The crude p-[4-[2-(trans-4-pentylcyclohexyl)ethylidene]cyclohexyl]benzoic acid obtained (3.6 g) was dissolved in 500 ml of ethanol and 125 ml of toluene and hydrogenated with 0.6 g of palladium/carbon (10%) for 48 hours at room temperature and normal pressure. The catalyst was filtered off and the filtrate was concentrated, thereby yielding 3.1 g of crude solid p-[trans-4-[2-(trans-4-pentylcyclohexyl)ethyl]cyclohexyl]benzoic acid.

(g) A mixture of 3.1 g of crude p-[trans-4-[2-(trans-4-pentylcyclohexyl)ethyl]cyclohexyl]benzoic acid, 50 ml of benzene and 0.9 ml of thionyl chloride was heated to boiling for 2 hours. Benzene and excess thionyl chloride were distilled off in vacuo. The residue was taken up twice in 50 ml of toluene and concentrated each time. The crude acid chloride obtained (3.5 g) was dissolved in 50 ml of dioxan and the solution was allowed to flow into a mixture of 18 ml of concentrated ammonia and 75 ml of dioxan. The resulting suspension was stirred at room temperature for 1 hour, then diluted with water and suction filtered. The material on the suction filter was washed neutral with water and then dried by concentration with toluene. 2.6 g of crude p-[trans-4-[2-(trans-4-pentylcyclohexyl)ethyl]cyclohexyl]benzamide were obtained.

The following compound was manufactured in an analogous manner:

p-[Trans-4-[2-(trans-4-propylcyclohexyl)ethyl]cyclohexyl]benzonitrile; m.p. (C—N) 85.7° C., cl.p. (N—I) 197.5° C.

We claim:

1. A compound of the formula

wherein ring A is 1,4-phenylene or trans-1,4-cyclohexylene, and $R^1$ is straight-chain $C_1$–$C_{12}$-alkyl or when positioned on a 1,4-phenylene ring $R^1$ may also be straight chain $C_1$–$C_{12}$-alkoxy.

2. The compound of claim 1, wherein $R^1$ is straight-chain $C_1$–$C_7$-alkyl or when positioned on a 1,4-phenylene ring $R^1$ may also be straight chain $C_1$–$C_6$-alkoxy.

3. The compound of claim 1, wherein $R^1$ is straight chain $C_1$–$C_{12}$ alkyl.

4. The compound of claim 3 wherein $R^1$ is a straight chain $C_1$–$C_7$ alkyl.

5. A liquid crystalline mixture comprising at least two components, at least one of said components is a compound of the formula:

wherein
ring A is 1,4-phenylene or trans-1,4-cyclohexylene, and
$R^1$ is straight-chain $C_1$–$C_{12}$ alkyl or when positioned on a 1,4-phenylene ring $R^1$ may also be straight-chain $C_1$–$C_{12}$-alkoxy.

6. An electro optical cell comprising:
(a) two plate means;
(b) a liquid crystal means disposed between the two plate means and including a compound of the formula:

wherein
ring A is 1,4-phenylene or trans-1,4-cyclohexylene, and
$R^1$ is straight chain $C_1$–$C_{12}$-alkyl or when positioned on a 1,4-phenylene ring $R^1$ may also be straight chain $C_1$–$C_{12}$-alkoxy; and
(c) means for applying an electrical potential to said plate means.